Nov. 8, 1932. E. A. MANDA Plant Pat. 43
FREESIA
Filed Sept. 17, 1931
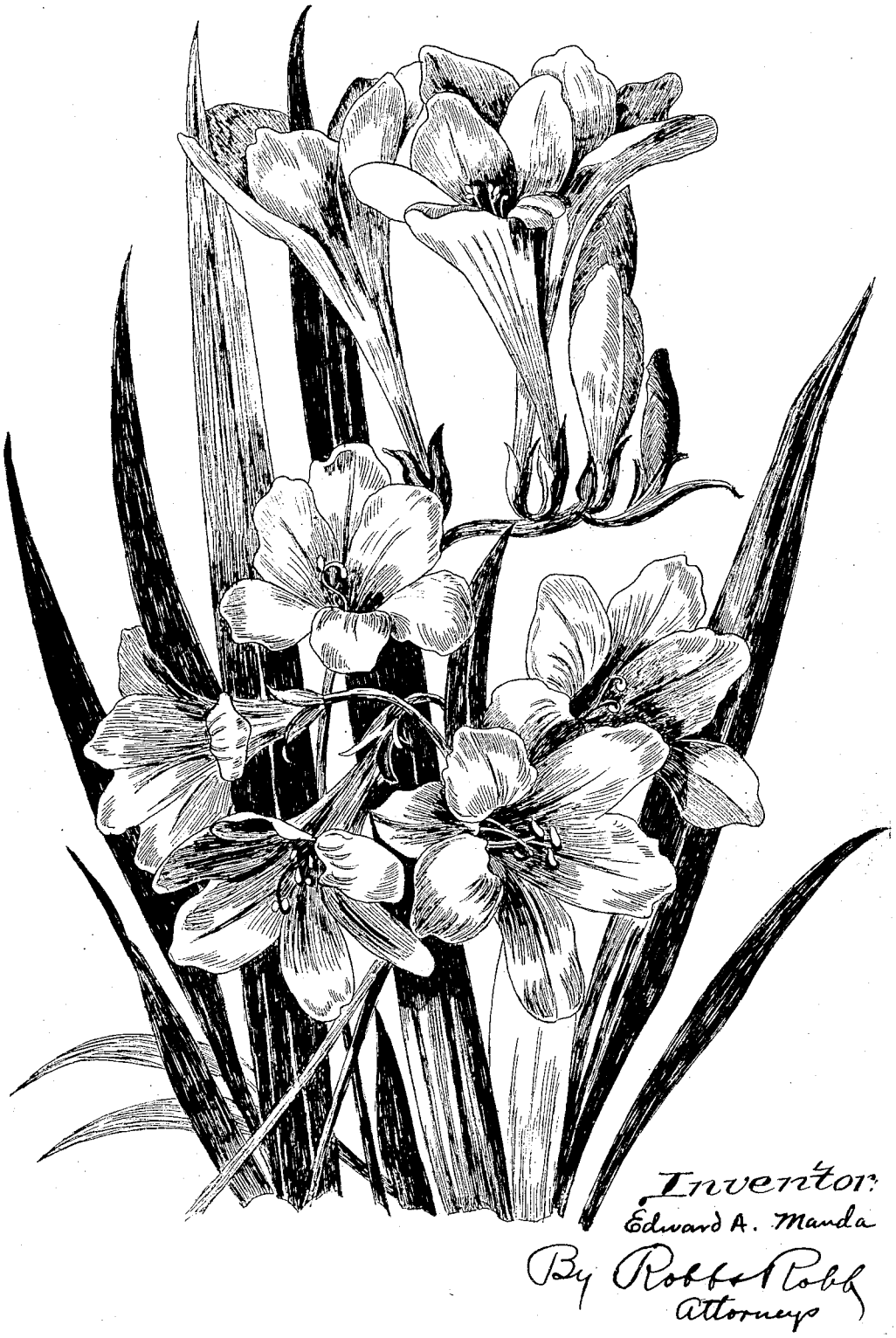
Inventor:
Edward A. Manda
By Robert Robb
Attorneys Patented Nov. 8, 1932

Plant Pat. 43

UNITED STATES PATENT OFFICE

EDWARD A. MANDA, OF EAST ORANGE, NEW JERSEY

FREESIA

Application filed September 17, 1931. Serial No. 563,632.

The present plant improvement relates to the well-known, popular cormous specie of flower generally called freesia, a much prized florist plant, easily grown and especially attractive as a window display.

By hybridization this plant has been greatly improved in many respects, as more particularly pointed out in the following description and comparison with possibly the best known variety now on the market.

The present freesia is a novel and distinct variety produced by a cross of freesia refracta alba and freesia yellow major and is characterized by its very early flowering,—much earlier than the known Elder's giant white variety. It flowers in January.

The drawing shows a typical specimen of the growth and grouping of flowers of my present improvements.

More specifically describing the plant, the improvement is characterized by its strongly erect growth, averaging from two and one-half to three feet, from an ovoid reticulated corm, the corms being large and averaging about one inch in diameter. The smaller corms are approximately three-eights of an inch in diameter, giving good representative flowers. This freesia will also form a good number of cormlets and unlike the majority will produce cormbils on the stem.

The stem is quite branched having as many as three or four lateral flower rachis, and bearing from eight to ten leaves, linear and very firm from thirty to sixty inches long by one-half inch wide.

The flowers are arranged in secund spikes on flexuose rachis; the perianth is pure white and approximately three inches long, the tube being unrestricted and gracefully tapering from the tip of the petals to the top of the ovary. The open floral segments are broad and overlapping, while yet lying flat (not cupped as in other varieties) at right angles to the tube. The substance is very firm. The reproductive organs are both sterile and impotent. There are seven flowers to each rachis.

By comparison with the best known variety, Elder's giant, I note the following distinctions: the tube is unrestricted, flower opening flat, of firm texture, stronger growth, longer stem, and the flowers three and more inches in diameter as compared with the restricted tube, cupped flower, infirm texture and smaller diameter flowers (two to two and one-half inches) of the Elder's giant.

I claim:

A freesia as herein shown and described, characterized by its long pure white, gracefully tapering perianth and flat opening floral segments.

In testimony whereof I affix my signature.

EDWARD A. MANDA.